United States Patent [19]

Greene et al.

[11] 4,142,059
[45] Feb. 27, 1979

[54] SPRAY DRYING SODIUM AND POTASSIUM 2-ETHYLHEXANOATE

[75] Inventors: James M. Greene; Sigmund A. Schildcrout; Gary D. Zintgraff, all of Indianapolis, Ind.

[73] Assignee: Eli Lilly and Company, Indianapolis, Ind.

[21] Appl. No.: 820,288

[22] Filed: Jul. 29, 1977

Related U.S. Application Data

[63] Continuation of Ser. No. 672,910, Apr. 2, 1976, abandoned.

[51] Int. Cl.$^2$ .............................................. C07C 51/42
[52] U.S. Cl. .................................................... 562/606
[58] Field of Search ........................................ 260/540

[56] References Cited

U.S. PATENT DOCUMENTS

| 2,895,990 | 7/1959 | Larrison et al. ............ 260/540 |
| 3,529,018 | 9/1970 | Anderson ...................... 260/540 |

FOREIGN PATENT DOCUMENTS 1381418  1/1975  United Kingdom .................. 260/541

Primary Examiner—Vivian Garner
Attorney, Agent, or Firm—Charles W. Ashbrook; Everet F. Smith

[57] ABSTRACT

An aqueous solution of sodium or potassium 2-ethylhexanoate is spray dried in a spray drier having an inlet temperature ranging from about 100° C. to about 160° C. and an outlet temperature ranging from 60° C. to about 130° C. to provide the corresponding sodium or potassium 2-ethylhexanoate having a moisture content of from about 0.5 to about 5.0 percent by weight and having improved purity and crystalline texture.

4 Claims, No Drawings

4,142,059

SPRAY DRYING SODIUM AND POTASSIUM 2-ETHYLHEXANOATE

This is a continuation, of application Ser. No. 672,910, filed Apr. 2, 1976, now abandoned.

BACKGROUND OF THE DISCLOSURE

A major use of sodium and potassium alkali metal salts of 2-ethylhexanoic acid is in the conversion of higher molecular weight organic acids to the corresponding salt of such acid by metathesis. For example, because sodium and potassium 2-ethylhexanoate generally are highly soluble in common organic solvents such as methanol, ethanol, acetone, and the like, it is a convenient process to add such salt to an organic solutiion of a higher molecular weight organic acid, thereby converting the higher molecular weight organic acid to the corresponding salt. The salt of such higher molecular weight acid so formed normally crystallizes out of the organic solution, leaving any unused reactants and by-products still in solution. Such process for salt formation is of particular importance in the case of hard to purify organic acids such as penicillanic acid and cephalosporanic acid antibiotics. U.S. Pat. No. 3,928,592, for instance, describes the reaction of sodium 2-ethylhexanoate with the hard to purify 7-(D-2-formyloxy-2-phenylacetamido)-3- (1-methyl-1H-tetrazole-5-ylthiomethyl)-3-cephem-4-carboxylic acid to provide the corresponding sodium salt of such acid in the form of a highly crystalline pure solid.

In order to effectively utilize either sodium or potassium 2-ethylhexanoate in the aforementioned metathetic reactions, it is important that such salts be of a high purity themselves, and of an easily handled character. Heretofore, the preparation of such alkali metal salts has been accomplished by simply titrating an aqueous solution of the alkanoic acid with the appropriate alkali metal hydroxide, and then adding to the aqueous solution a suitable organic anti-solvent in order to force the alkanoic acid salt out of solution and into a solid form. Such process suffers from various drawbacks, including high cost due to the use of organic anti-solvents and safety hazards resulting from working with large volumes of such solvents. Even more serious drawbacks of such process, however, include the nature of the sodium and potassium 2-ethylhexanoate so formed, which salts typically are impure and of a poor physical character in that the precipitated solid normally is tacky, of undesirable crystalline form, hard to dry, and generally difficult to manage, especially on a commercial scale, due to its extreme hygroscopic properties.

Other processes for preparing the sodium and potassium salts of 2-ethylhexanoic acid include freeze drying an aqueous solution of such salt. This method is commercially unfeasible, however, since an aqueous solution containing about fifty percent by weight of sodium or potassium 2-ethylhexanoate fails to remain frozen under normal freeze-drying conditions. Simple tray-drying of such aqueous solutions is commercially unfeasible due to the extreme length of time required to effect dehydration, and more importantly because such process fails to provide a product of acceptable crystalline quality.

A process for preparing sodium and potassium 2-ethylhexanoate having improved purity and crystalline character, in addition to having improved handleability, and thus obviating the problems of the prior art processes, has now been invented and is the subject of this disclosure.

SUMMARY OF THE INVENTION

Crystalline sodium and potassium 2-ethylhexanoate of high purity are prepared by spray drying an aqueous solution containing from about 40 percent by weight to about 70 percent by weight of sodium 2-ethylhexanoate or potassium 2-ethylhexanoate respectively. The aqueous solution is atomized to form a fine mist of aqueous sodium 2-ethylhexanoate or potassium 2-ethylhexanoate, such fine mist then is passed through a stream of air having a temperature of about 100° C. to about 160° C. so as to evaporate the water from the aqueous solution, thus leaving a dry crystalline product having a moisture content ranging from about 0.5 percent by weight to about 5.0 percent by weight. Such product is non-tacky and easily handled.

DETAILED DESCRIPTION OF THE INVENTION

Spray drying typically is a process which involves the rapid dehydration of moist particles which contain solids in either the soluble or insoluble form or both. The extent of successful drying and formation of a crystalline product normally depends upon several factors, including the temperature range of the spray drier, the concentration of the solution undergoing the drying process, and the extent of atomization of the solution which has been preimposed on the feedstock to create the aforementioned moist particles. Deterrents to successful spray drying include a high viscosity of the solution being atomized, in addition to operational temperature. It is therefore important in any particular spray drying process to utilize optimum concentrations of solutions being dried, and optimum temperature ranges for the desired result.

According to the process of the present invention, an aqueous solution containing preferably from about 40 percent by weight to about 70 percent by weight of a salt selected from sodium 2-ethylhexanoate and potassium 2-ethylhexanoate is atomized in a conventional spray drying apparatus. For instance, aqueous solutions containing from about 50 percent by weight to about 65 percent by weight of sodium 2-ethylhexanoate can be spray dried. Such aqueous solutions of sodium 2-ethylhexanoate or potassium 2-ethylhexanoate generally are prepared by mixing equimolar amounts of 2-ethylhexanoic acid with sodium hydroxide or potassium hydroxide in a given amount of water. Typical of the spray drying apparatus which can be utilized in carrying out the process according to this invention is that supplied by the Komline-Sanderson Engineering Corporation of Peapock, New Jersey, or alternatively the Bowen Spray Drier. The preferred temperature range for the spray drying process is from about 60° C. to about 160° C. A stream of air is heated, typically by a direct gas-fired or oil-fired burner, electric coils, steam or the like, to a temperature of from about 100° C. to about 160° C., preferably from about 110° C. to about 150° C., and introduced into the conventional spray drying apparatus as the inlet air. The heated air stream will pass over a fine mist or atomized stream of the above-mentioned aqueous solution of sodium or potassium 2-ethylhexanoate. Such atomization generally is accomplished by conventional methods, for example by passing the aqueous solution through a spray nozzle or pouring a stream of the solution onto a centrifugal atomizer such as a spinning disc rotating at a speed of about 5000 to 8000 revolutions per minute. The rate at which the aqueous solution is introduced into the spray drier can be varied over a wide range. Such feed rate generally will be from about 50 to about 500 ml. of solution per minute; however, the feed rate can be increased if desired to about 800 ml. per minute in commerical spray drying processes. Such feed rate will provide from about 3 to about 20 kg. of dried product per hour. The aforementioned stream of heated drying air will cool during the drying process, the extent of such cooling being determined to some extent by the feed rate of the aqueous solution being spray dried and the inlet temperature. It is preferred that the heated drying air cools to the extent that the outlet temperature is within the range of from about 60° C. to about 130° C., preferably from about 90° C. to about 115° C. Such outlet temperature can be maintained by variations in the inlet temperature and the feed rate as hereinbefore described. The sodium or potassium 2-ethylhexanoate which is thus formed is a crystalline solid having a moisture content ranging from about 0.5 percent by weight to about 5.0 percent by weight. The product so formed is not tacky and is easily handled in contrast to such products prepared by the prior art processes. The product so formed is simply collected from the spray drying apparatus and is ready for use as desired without further purification. The yield of the solid sodium or potassium 2-ethylhexanoate so formed typically ranges from about 70 to about 97 percent.

The product produced according to the process conditions set forth above has improved purity and enhanced crystalline characteristics when compared to products made by the prior art processes described hereinabove. The spray dried products are not tacky, are easily handled even on large scales, and are readily soluble in water, ethanol, and acetone. Of four samples of 9.7 grams each of spray dried sodium 2-ethylhexanoate, each completely dissolved in 100 ml. of acetone in fifteen minutes or less. When 10 ml. of each of such acetone solutions were diluted with 25 ml. of water and their respective pH values checked, it was determined that the pH ranged from 8.2 to 8.5. The density of sodium 2-ethylhexanoate prepared according to this invention is about 0.30 gm./cc.

The process provided by this invention is further illustrated by the following detailed experimental results. The examples are intended merely to illustrate the practice of the invention, and are not to be construed as limiting in any way.

EXAMPLE 1

Preparation of sodium 2-ethylhexanoate for Spray drying

A solution of 240 g. of sodium hydroxide in 450 ml. of water was stirred and cooled in an ice-water bath to 20° C. while 875 g. of 2-ethylhexanoic acid was added dropwise to the reaction mixture over thirty minutes. The temperature of the reaction mixture was maintained at or below 70° C. by cooling in an ice-water bath. After the addition of the 2-ethylhexanoic acid was complete, the reaction mixture was stirred for one hour. The aqueous solution so formed was a 63.5 percent by weight solution of sodium 2-ethylhexanoate and was suitable for spray drying according to this invention.

EXAMPLE 2

The 63.5 percent by weight solution of sodium 2-ethylhexanoate in water from Example 1 was atomized through a spray nozzle into a spray drying apparatus having an inlet air temperature of about 118° to about 138° C. The aqueous solution was introduced into the spray dryer at a feed rate of about 0.3 to about 0.5 gallons per minute, and was monitored by a standard Rotometer. The outlet temperature was recorded at about 107° C., as controlled for instance by adjusting the inlet air temperature and the feed rate. The sodium 2-ethylhexanoate was collected from the bottom of the spray dryer and packaged for use as desired.

EXAMPLE 3

An aqueous solution containing 63.5 percent by weight of sodium 2-ethylhexanoate was atomized through a spray nozzle under 80 pounds of pressure into a Komline-Sanderson Spray Dryer having an inlet temperature of about 112° C. at a feed rate of 136 ml. per minute. The total volume of solution fed into the spray drier was 993 ml. The outlet temperature was recorded at about 85° C. The product, a white crystalline form of sodium 2-ethylhexanoate, was recovered from the chamber and cyclone of the spray drier, and amounted to 411 grams, a 74.9 percent recovery. The sodium 2-ethylhexanoate so obtained contained 3.57 percent by weight of water as determined by Karl-Fischer analysis.

We claim:

1. A process for preparing a purified non-tacky crystalline salt selected from sodium 2-ethylhexanoate and potassium 2-ethylhexanoate comprising spray drying an aqueous solution containing from about 40 percent by weight to about 70 percent by weight of sodium 2-ethylhexanoate or potassium 2-ethylhexanoate respectively in a spray dryer having a temperature range of about 60° C. to about 160° C., and a feed rate of from about 50 to about 500 ml. per minute, and collecting the purified crystalline salt having a moisture content ranging from about 0.5 percent by weight to about 5.0 percent by weight therefrom.

2. The process according to claim 1 wherein an aqueous solution containing sodium 2-ethylhexanoate is spray dried in a spray dryer having an inlet air temperature of from about 100° C. to about 160° C. and an outlet air temperature of about 60° C. to about 130° C.

3. The process according to claim 2 wherein an aqueous solution containing from about 50 percent by weight to about 65 percent by weight of sodium 2-ethylhexanoate is spray dried.

4. The process according to claim 3 wherein the inlet temperature of the spray dryer ranges from about 110° C. to about 150° C. and the outlet temperature ranges from about 90° C. to about 115° C.

* * * * *